United States Patent
Brianza

(10) Patent No.: US 10,610,275 B2
(45) Date of Patent: Apr. 7, 2020

(54) DEVICE FOR VARIABLE FIXATION OF BONE FRAGMENTS

(71) Applicant: Biomech Innovations SA, Nidau (CH)

(72) Inventor: Stefano Brianza, Basel (CH)

(73) Assignee: Biomech Innovations SA, Nidau (CH)

( * ) Notice: Subject to any disclaimer, the term of this patent is extended or adjusted under 35 U.S.C. 154(b) by 4 days.

(21) Appl. No.: 15/547,780

(22) PCT Filed: Jan. 28, 2016

(86) PCT No.: PCT/IB2016/050445
§ 371 (c)(1),
(2) Date: Jul. 31, 2017

(87) PCT Pub. No.: WO2016/125054
PCT Pub. Date: Aug. 11, 2016

(65) Prior Publication Data
US 2018/0263674 A1     Sep. 20, 2018

(30) Foreign Application Priority Data

Feb. 3, 2015 (CH) .................................. 00148/15

(51) Int. Cl.
*A61B 17/86* (2006.01)
*A61B 17/80* (2006.01)

(52) U.S. Cl.
CPC .......... *A61B 17/866* (2013.01); *A61B 17/863* (2013.01); *A61B 17/8605* (2013.01); *A61B 17/8057* (2013.01); *A61B 2017/8655* (2013.01)

(58) Field of Classification Search
CPC . A61B 17/80; A61B 17/8052; A61B 17/8057; A61B 17/84; A61B 17/86;

(Continued)

(56) References Cited

U.S. PATENT DOCUMENTS

| 4,338,926 A | 7/1982 | Kummer et al. |
| 4,655,203 A | 4/1987 | Tormala et al. |

(Continued)

FOREIGN PATENT DOCUMENTS

| EP | 2740428 | 6/2014 |
| WO | WO 2010/111350 | 9/2010 |

OTHER PUBLICATIONS

Lujan et al. Locked plating of distal femur fractures leads to inconsistent and asymmetric callus formation. J Orthop Trauma. Mar. 2010;24(3):156-62.

(Continued)

*Primary Examiner* — Eric S Gibson
(74) *Attorney, Agent, or Firm* — Knobbe, Martens, Olson & Bear LLP

(57) ABSTRACT

Device for bone fixation with a head portion (5), a tapering front portion (8) and a shaft (3) between said head portion (5) and said tapering front portion (8), said shaft (3) having a distal portion (3a) adjacent to said tapering front portion (8) and a proximal portion (3b) adjacent to said head portion (5); whereby said distal portion (3a) being provided with a thread and having a constant outer diameter $D_A$ and an inner core diameter $D_I$; at least the proximal portion (3b) of said shaft (3) has a core (2) consisting of a biologically non-degradable material with degradation rate BND and having a diameter $d \leq D_I$; a sleeve (9) surrounding said core and consisting of a biologically degradable material with degradation rate BD, whereby BD>BND and said sleeve (9) being fixed to said core in a non-rotatable manner.

16 Claims, 2 Drawing Sheets

(58) Field of Classification Search
CPC .............. A61B 17/8605; A61B 17/861; A61B 17/8615; A61B 17/862; A61B 17/8625; A61B 17/863; A61B 17/8635; A61B 17/864; A61B 17/866
See application file for complete search history.

(56) References Cited

U.S. PATENT DOCUMENTS

| | | | |
|---|---|---|---|
| 4,756,307 A | 7/1988 | Crowninshield | |
| 4,773,406 A | 9/1988 | Spector et al. | |
| 5,013,315 A | 5/1991 | Barrows | |
| 5,061,137 A * | 10/1991 | Gourd | F16B 19/00 411/392 |
| 5,411,523 A * | 5/1995 | Goble | A61B 17/0401 606/104 |
| 6,423,062 B2 * | 7/2002 | Enayati | A61B 17/8635 606/318 |
| 6,471,707 B1 | 10/2002 | Miller et al. | |
| 6,537,070 B1 * | 3/2003 | Stucki-McCormick | A61B 17/666 433/173 |
| 8,114,141 B2 | 2/2012 | Appenzeller et al. | |
| 8,506,608 B2 | 8/2013 | Cerynik et al. | |
| 9,023,088 B2 * | 5/2015 | Voisard | A61B 17/0401 606/313 |
| 9,339,316 B2 * | 5/2016 | Hulliger | A61B 17/84 |
| 10,172,656 B1 * | 1/2019 | Reimels | A61B 17/844 |
| 2002/0150444 A1 * | 10/2002 | Mhaimeed | F16B 7/185 411/383 |
| 2003/0133769 A1 * | 7/2003 | Schultz | B25B 13/065 411/403 |
| 2004/0030341 A1 * | 2/2004 | Aeschlimann | A61B 17/00491 606/232 |
| 2006/0106390 A1 * | 5/2006 | Jensen | A61B 17/8685 606/318 |
| 2006/0195099 A1 * | 8/2006 | Bottlang | A61B 17/863 606/67 |
| 2007/0233073 A1 | 10/2007 | Wisnewski et al. | |
| 2008/0188899 A1 * | 8/2008 | Bottlang | A61B 17/8057 606/308 |
| 2008/0317812 A1 | 12/2008 | Zhang et al. | |
| 2009/0099610 A1 | 4/2009 | Johnson et al. | |
| 2009/0157123 A1 * | 6/2009 | Appenzeller | A61B 17/68 606/301 |
| 2010/0023057 A1 * | 1/2010 | Aeschlimann | A61B 17/0401 606/246 |
| 2010/0036441 A1 * | 2/2010 | Procter | A61B 17/80 606/329 |
| 2012/0029564 A1 | 2/2012 | Trieu et al. | |
| 2012/0029579 A1 | 2/2012 | Bottlang et al. | |
| 2012/0034046 A1 * | 2/2012 | Cooper | F16B 35/041 411/361 |
| 2012/0078369 A1 * | 3/2012 | Hart | A61B 17/686 623/13.14 |
| 2012/0089175 A1 * | 4/2012 | LeCronier | A61B 17/686 606/205 |
| 2013/0245697 A1 * | 9/2013 | Hulliger | A61B 17/84 606/281 |
| 2014/0005731 A1 * | 1/2014 | Biedermann | A61B 17/686 606/328 |
| 2014/0094860 A1 * | 4/2014 | Reimels | A61B 17/8685 606/323 |
| 2014/0172026 A1 * | 6/2014 | Biedermann | A61B 17/844 606/326 |
| 2018/0085154 A1 * | 3/2018 | Kulper | A61B 17/0401 |
| 2018/0214192 A1 * | 8/2018 | Roby | A61B 17/866 |
| 2018/0263674 A1 * | 9/2018 | Brianza | A61B 17/863 |

OTHER PUBLICATIONS

International Search Report and Written Opinion in PCT App. No. PCT/IB2016/050445 dated Apr. 27, 2016 in 12 pages.

* cited by examiner

DEVICE FOR VARIABLE FIXATION OF BONE FRAGMENTS

This application is the U.S. National Stage of PCT/IB2016/050445 filed on Jan. 28, 2016, which in turn claims foreign priority to Switzerland Patent App. No. CH 00148/15 filed on Feb. 3, 2015. All of the above applications are incorporated by reference herein in their entirety and are to be considered a part of this specification. Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The invention relates to a bone fixation device according to the preamble of claim 1. It relates in general to the field of medical devices used to treat bone fractures. In particular, it relates, but is not limited, to a bone screw with features and/or attributes to provide a variable fixation to bone fragments during the fracture healing period.

2. Description of the Related Art

The skeleton responds to changes in strain adjusting its bone mass and distribution in order to restore the optimal local strain level. Under favorable boundary conditions, a bone fracture is followed by either the primary or secondary repair process in which the anatomical and functional skeletal element capability is restored through different phases. These repair processes as well are modulated by changes in the mechanical environment.

Since more than 50 years, bone fracture treatment is routinely carried out through intramedullary, extramedullary internal or external load carriers such as, for example, nails, bone plates, etc., when necessary used in combination with fixation elements like in e.g. bone screws in order to provide to the bone fragments the stability promoting one of the repair processes. Later on, a variety of bone fixation devices featuring the association of a resorbable/degradable and a non-resorbable material have been invented to progressively load at a late stage in the healing process the treated bone/bone fragments taking advantage of the molecular weight decrease, reduction in mechanical strength and finally mass loss phases a resorbable/degradable material undergoes once implanted. The aim was stress shielding decrease (U.S. Pat. Nos. 4,756,307A, 4,655,203A, 4,338,926, 4,773,406A, 5,013,315A), or to vary the stability among the different parts of a compound (U.S. Pat. No. 8,506,608, US2007233073A1, US2008317812A1) or composite medical device (US2012029564A1).

From U.S. Pat. No. 8,506,608 CERYNIK ET AL. an orthopedic screw for use in a fixation device for treating fractures is known. The known screw has a sleeve of bioresorbable material surrounding the screw shaft and fixed thereto, whereby the diameter of the sleeve is larger than the diameter of the shaft.

The aim of CERYNIK ET AL. is to change the properties of the compound fixation device through modifying the performance of the plate to screw connection, namely to change the locking mechanism between screw and plate to become a non-locking mechanism over time. The function of gradually bringing additional strain to the callus just under the plate is not purposeful. With the polymer resorption the plate/screw construct goes from locking to non-locking and therefore the positive aspects of the locking stability are lost for the remaining period of treatment.

There remains therefore the need for a device for bone fixation allowing decreasing gradually the stiffness of the bone-implants construct without losing the benefit of the locking fixation until the bone plate is removed. Lately, some fixation elements have been invented in order to provide through dynamic or far cortical locking a flexible engagement to the fractured bone fragments (U.S. Pat. No. 8,114,141B2, US2006195099A1, US2012029579A1) at an early stage of fracture treatment. This dynamisation or additional flexibility is fully provided at the beginning of the fracture treatment and doesn't change during the medical treatment.

BRIEF SUMMARY OF THE INVENTION

It is therefore an object of the invention to provide a bone fixation device which allows progressively more interfragmentary motion during time.

The invention solves the posed problem with a device for bone fixation comprising the features of claim 1 which allows gradually modifying the resistance offered by the bone fixation device against bone interfragmentary motion during fracture treatment.

The device for variable fixation of bone fragments (device for bone fixation) features materials that are biologically degradable and biologically non-degradable according to claim 1, arranged in way to provide a stable but variable fixation to bone fragments. The use of the device for bone fixation to treat bone fractures is intended to promote healing through a progressive change of the stability provided to the bone fragments. This gradual change is intended to stimulate tissue differentiation through mechano-biologically mediated pathways.

The bone fixation device according to the invention is a composite implant comprising a biologically non-degradable material and a biologically degradable.

The degradation rate of a material and the definition of biologically degradable and non-biologically degradable materials are intended in this invention in relation to the time period necessary to gain bone fracture healing. Accordingly, a material featuring a degradation rate BD is defined as one substantially decreasing its mechanical properties when exposed to extracellular body fluids (featuring physiological and fracture characteristic volume, pH, ions and proteins concentration) during the fracture healing timeframe (in e.g. but not limited to short term bioresorbable polymers). On the other side a material featuring a degradation rate BND is defined as a material not substantially decreasing its mechanical properties when exposed to similar extracellular fluids during the fracture healing timeframe (in e.g. but not limited to long term bioresorbable polymers and metals).

The bone fixation device according to the invention offers the following advantages compared with the prior art CERYNIK:

1) With the polymer resorption in CERYNIK the construct goes from a locking to a non-locking construct. The positive aspects of the locking stability are thus lost for the remaining part of the treatment. However, the advantage of the present invention is to be seen in the matter of gradually increasing of the interfragmentary displacement without losing the benefit of the locking fixation. The bone-implants construct becomes less stiff not loose.
2) Going from locking to non-locking in CERYNIK the relative fragments displacement, when these were not fused yet, could slightly increase with time. However, the trajectories of the fragments displacements will be almost the same between the locking and non-locking configurations. According to the device of the present invention the trajectory of the fragments changes with time allowing stimulating more the cortex under the plate (cis cortex). The lack of callus formation under the plate has been reported as a clinical problem (Lujan et al. Locked plating of distal femur fractures leads to inconsistent and asymmetric callus formation. J Orthop Trauma. 2010 March; 24(3):156-62.).

3) The resorption in CERYNIK is meant to take place at a late stage of fracture healing. It is meant to decrease the stress shielding problem. However, according to the device of the present invention the decrease of mechanical properties of the biologically degradable material mainly occurs early in the fracture treatment so to gradually stimulate the callus formation. At the same time, once the mechanical properties of the biologically degradable material have substantially changed, the lost screw purchase in the cis cortex will allow reducing stress shielding as well.

Further advantageous embodiments of the invention can be commented as follows:

In an additional embodiment of the invention the sleeve has a constant outer diameter being smaller than the outer diameter of the thread provided in the distal portion of the device.

In a further embodiment the sleeve has a constant outer diameter being greater than the outer diameter of the thread provided in the distal portion of the device.

In yet a further embodiment the sleeve has a constant outer diameter being equal to the outer diameter of the thread provided in the distal portion of the device.

In a further embodiment the diameter of the core of the proximal portion of the shaft is smaller than the inner core diameter of the distal portion of the shaft.

In an additional embodiment the sleeve of the device is provided with a macrostructuring (e.g. an outer thread, partial threads, lips or peripheral grooves).

In another embodiment the sleeve of the device has a smooth outer device.

Whatever is the loading applied to the bone the sleeve will be squeezed between the metal core and the wall of the hole in the bone. The higher the modulus the higher the resistance offered to this squeezing and thus the smaller will be the bone fragments relative displacement.

In another embodiment lies the ratio of the diameter of the core relative to the outer diameter of the distal portion of the device in the range between 0.6 and 0.9.

In an additional embodiment the distal portion of the device for bone fixation consists of a biologically non-degradable material.

The allowed maximum relative displacement between the biologically non-degradable part of the device for bone fixation (core, proximal portion 3b) and the inner side of the bone hole in the near (cis) cortex, once the degradation of the material of the biologically degradable sleeve is completed, ranges preferably between 5 and 10% of the outer diameter $D_A$ of the thread of the distal portion. The thickness of the biologically degradable sleeve and the degradation rate of the sleeve material can be however different according to the indication for use.

In a further embodiment the thread being provided in the distal portion of the device is not continuous, i.e. the pitch of the thread may vary and/or the helical structure of the thread can be disconnected due to e.g. flutes.

In an additional embodiment the sleeve comprises a resorbable material.

In a further embodiment the sleeve comprises a material having an initial compression modulus in the range of 0.5-20 GPa, preferably in the ranges of 0.5-3.0 GPa and/or 12-17 GPa.

In yet another embodiment of the invention the molecular weight of the resorbable material is reduced by 50% in the time period between one to three weeks, preferably by 90% in the time period between six to nine weeks.

In a further embodiment the compression strength of the resorbable material is reduced by 50% in the time period between four to eight weeks, preferably by 90% in the time period ten to fourteen weeks.

In another embodiment the elastic modulus of the resorbable material is reduced by 50% in the time period between four to eight weeks, preferably by 90% in the time period ten to fourteen weeks.

After a period of initial stability of roughly one week, the material hydrolytically or enzymatically loses in maximum about 12-14 weeks most of its molecular weight and strength allowing more relative displacement between the fixation element axis and the bone immediately surrounding the sleeve.

The biologically degradable material is a synthetic or natural, dense or porous biocompatible one, hydrolytically and/or enzymatically changing its mechanical properties during the fracture healing period thanks to physiological processes or to external sources of energy. Among these polymeric materials and/or polymer-glass/ceramic materials including but not limited to poly (glycolic acid) (PGA), polylactic acid (PLA) in its stereoisomeric forms that give rise to four morphologically distinct polymers (D,L,DL, meso), Poly(dioxanone) (PDS), poly-L-lactic-co-glycolic acid (PLGA), poly-D/L-lactic acid, poly-L-lactic acid), polycaprolactone (PLC), polycaprolactone-calcium phosphate (PCL-CaP), poly(L-lactide-co-D,L-lactide) (PLADLA or PLDLLA) and combination thereof in different ratios.

In a further embodiment the biologically degradable material of the sleeve comprises one or more of the following materials: copolymeric lactic glycolic acid at different ratios, degradable self-expanding poly-L,D-Lactide and poly-ε-caprolactone homopolymers.

In an additional embodiment the sleeve comprises hydroxyapatite and/or β-tricalcium phosphate.

The characteristics and distribution of the materials provide at least one additional function to the bone fixation device. Namely, once implanted, before fracture healing, for a given force or moment applied to the fractured bone, they allow modifying during time the relative motion between two or more bone fragments. Additionally, when still implanted, after X-rays investigations show fracture gap closure, for a given force or moment applied to the bone they allow straining the bone tissue in the area where the medical device is implanted. The expected outcome of these functions is an improvement in fracture healing process triggering, promoting fracture healing, stimulating callus formation at the cis cortex and decreasing stress shielding in the treated bone area.

In a further embodiment the biologically non-degradable material of the core comprises one or more of the following materials: titanium, one of the titanium alloys (in e.g. Ti-6Al-4V or Ti-6Al-7Ni), stainless steel, metal alloys (CoCr, CoCrMo, CoCrMoC, CoCrNi or CoCr—WNi) etc. or long term biodegradable polymers like but not limited to LPLA, PCI, PDO etc.

In an additional embodiment the distal portion of the shaft is provided with a hydroxyapatite coating by means of superficial treatments. This embodiment promotes osteointegration and increases fatigue resistance of the distal portion of the device.

In a particular embodiment of the invention the device is in the shape of a bone screw.

In an additional embodiment the device for bone fixation comprises a head having a diameter greater than the outer diameter of the thread of the distal portion.

In a further embodiment the screw head is conical.

The present invention also covers a kit for the treatment of bone fractures comprising a device for bone fixation according to the present invention and a bone plate with at least one locking plate hole having a locking mechanism allowing a stable fixation of the device for bone fixation within the bone plate. Among other methods, the stable fixation of the device for bone fixation in the plate hole is achievable by means of threads provided on the head of the device for bone fixation and on the inner surface of the hole, by a non-positive connection formed by a conical head of the device and the conical hole of the bone plate as well as by deformation of the head of the device within the hole of the plate or vice versa, namely deformation of the hole through the cutting thread on the screw head or any other method used to fully restrain a bone screw to a bone pate.

The present invention covers the use of the device according to the present invention for reconstruction of the musculoskeletal system.

A BRIEF DESCRIPTION OF THE DRAWINGS

Several embodiments of the invention will be described in the following by way of example and with reference to the accompanying drawings in which.

DETAILED DESCRIPTION OF THE INVENTION

The present invention generally concerns a surgical fixation device and methods used to provide bone fragments or bones having a stability such that the physiological healing process can take place when used in connection with plates featuring a locking mechanism. The device for bone fixation preferably includes a tapering front portion and a shaft between said head portion and said tapering front portion. The shaft has a distal portion being provided with a thread with a constant outer diameter and a proximal portion having a biologically non-degradable core and a biologically degradable sleeve surrounding said core. The biologically degradable material of the sleeve has an outer surface directly engaging the bone to initially fix the bone fragments according to the possible anatomical bone reconstruction.

For a given load or moment, the relative displacement of the bone fragments gradually increases with time upon degradation of the sleeve.

There are several possibilities to achieve fixation of the sleeve to the core in a non-rotatable manner, e.g.:

- The surface of the proximal portion 3b features cross sectional radial extrusions, longitudinally and discontinuously extending along the surface, gripping into the degradable material;
- The surface of the proximal portion 3b features cross sectional radial grooves, longitudinally and discontinuously extending along the surface, where the degradable material can grip into the non-degradable material;
- The surface of the proximal portion 3b features a rugosity such that it prevents the sleeve from rotating around the screw axis during screw insertion;
- A biocompatible adhesive glues the sleeve to the surface of the proximal portion 3b;
- The manufacturing processes imply the rise of a sleeve controlled radial shrinking.

Figure 1:
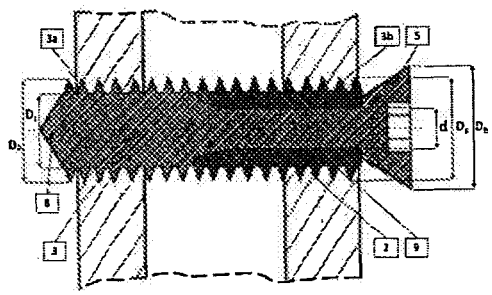
FIG. 1 shows a schematic view of a cortical screw according to the invention.

The invention and the additional embodiments of the invention are explained below with reference to the figures of several embodiments:

FIG. 1 shows a device for bone fixation in a form of a cortical screw with a head portion 5, a tapering front portion 8 and a shaft 3 between the head portion 5 and the tapering front portion 8. The shaft 3 has a distal portion 3a adjacent to the tapering front portion 8 and a proximal portion 3b adjacent to said head portion 5. The distal portion 3a has a threaded surface with a constant outer diameter $D_A$ and an inner core diameter $D_I$. The proximal portion 3b of the shaft 3 comprises a biologically non-degradable core 2 with the diameter d being smaller than the inner core diameter $D_I$ of the distal portion 3a and a biologically degradable sleeve 9 surrounding the core 2.

Figure 2:
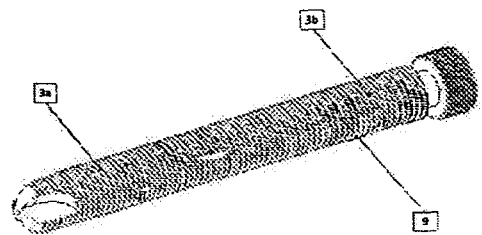
FIG. 2 shows a perspective view of a cortical screw according to the invention.

FIG. 2 shows a perspective view of the device according to the invention. The distal portion 3a as well as the outer surface of the sleeve 9 in proximal portion 3b of the device as shown in FIG. 2 are provided with outer threads.

The front portions of the embodiments shown in FIGS. 1 and 2 may incorporate self-cutting and self-tapping features which allow the screw insertion in the bone without the respective need for predrilling and for tapping. The distal portion 3a of the shaft 3 is configured to fix the screw in cortical bone in this specific case. The outer diameter $D_A$ of the distal portion 3a ranges between, but not limited to 1.5 mm and 8.0 mm. More specifically the device for bone fixation may have an outer diameter $D_A$ of approximately 1.5, 2.0, 2.4, 2.7, 3.5, 4.0, 4.5, 5.0, 6.5, 7.0, 7.3 and 8 mm). The device for bone fixation is typically 20 to 80 mm long. The relative length of the distal 3a and proximal 3b portions of the shaft 3 are generally similar but better defined according to the intended use accommodating for different bone sizes and anatomical characteristics so that, when the device for bone fixation is implanted, the distal portion 3a of the shaft 3 is engaging the far (trans) cortex, whereby the proximal portion 3b of the shaft 3 is placed within the near (cis) cortex). The biologically degradable material of the sleeve 9 surrounding the biologically non-degradable core of the proximal portion 3b of the shaft 3 is engaging the near (cis) cortex. The compound device stiffness is sufficient to provide the expected bending resistance under expected loading. At the junction between the biologically degradable material of the proximal portion 3b and the biologically non-degradable material of the distal portion 3a there is a middle portion of the shaft 3 being provided with backward cutting elements (e.g. cutting flutes) allowing easier removal of the device at the end of the treatment.

The distal portion 3a of the shaft 3 is provided with a thread having a constant outer diameter $D_A$ and an inner core diameter $D_I$. The proximal portion 3b of the shaft 3 comprises a core 2 of either fixed or variable diameter (could be used to restrain the sleeve and avoid rotation) and a sleeve 9 surrounding the core 2. The sleeve 9 is provided with a thread having an outer diameter Ds. According to the embodiments of the FIGS. 1 and 2 the outer diameter Ds of the sleeve 9 is identical to the outer diameter $D_A$ of the thread being provided in the distal portion 3a of the shaft 3.

Figure 3:
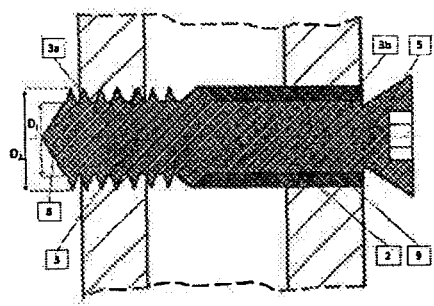
FIG. 3 shows a schematic view of another cortical screw according to the invention.

FIG. 3 shows another device for bone fixation in a form of a cortical screw with a head portion 5, a tapering front portion 8 and a shaft 3. The shaft 3 has a distal portion 3a adjacent to the tapering front portion 8 and a proximal portion 3b adjacent to said head portion 5. The distal portion 3a has a threaded surface with a constant outer diameter $D_A$ and an inner core diameter $D_I$. The proximal portion 3b of the shaft 3 comprises a core 2 having a diameter d=$D_I$ as well as a sleeve 9 surrounding the core 2. The outer surface of the sleeve 9 is not threaded. At the junction between the biologically degradable material of the sleeve 9 of the proximal portion 3b and the biologically non-degradable material of the distal portion 3a, there is a middle portion of the shaft 3 featuring forward and backward cutting elements respectively allowing removing of bone graft arising through insertion of the device for bone fixation and easier removal of the device at the end of the treatment.

In a further embodiment (not shown in the figures) the outer surface of the sleeve 9 of the proximal portion 3b can be partially threaded.

Figure 4:
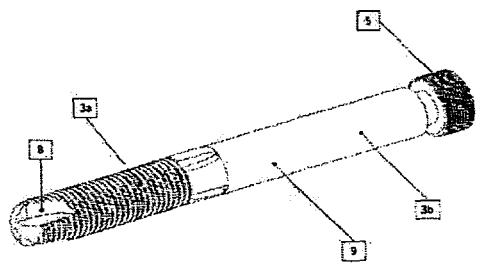
FIG. 4 shows a perspective view of another cortical screw according to the invention.

FIG. 4 shows a perspective view of the device according to the invention in a form of a cortical screw with a head portion 5, a tapering front portion 8 and a shaft 3. The shaft 3 has a distal portion 3a adjacent to the tapering front portion 8 and a proximal portion 3b adjacent to said head portion 5. The distal portion 3a has a threaded surface with a constant outer diameter $D_A$ and an inner core diameter $D_I$. The proximal portion 3b consists of the sleeve 9 consisting of a biologically degradable material and having a constant outer diameter. The sleeve 9 surrounds the core 2 consisting from a biologically non-degradable material.

Figure 5:
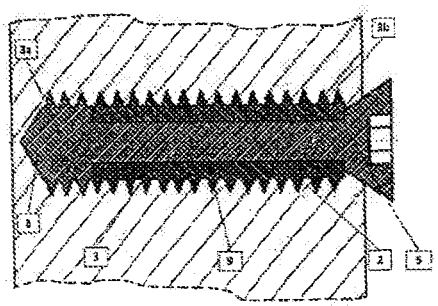
FIG. 5 shows a schematic view of a cancellous screw according to the invention.

FIG. 5 shows a schematic view of a device according to the invention. The cancellous screw as shown in FIG. 5 comprises a head portion 5, a tapering front portion 8 and a shaft 3 between the head portion 5 and the tapering front portion 8. The shaft 3 has a distal portion 3a adjacent to the tapering front portion 8 and a proximal portion 3b adjacent to said head portion 5.

This embodiment is indicated to fix bone fragments characterized by a large amount of cancellous bone surrounded by a shell of cortical bone. This device preferably includes a tapering front portion 8 and a shaft 3 between the head portion 5 and the tapering front portion 8. The tapering front portion features cutting flutes and it is configured to fix the screw in cancellous bone in this specific case. The shaft features a threaded, partially threaded or flat sleeve surface consisting of a biologically degradable material and having a constant outer diameter around the core 2 consisting of the biologically non-degradable material. The sleeve 9 features mechanical properties and degradation rate specifically tailored for cancellous bone fixation. This screw aims decreasing the stress at the bone to medical device interface and progressively redistributing the load transmission between the bone fragments through the sleeve degradation. At the junction between the biologically degradable material of the sleeve 9 and biologically non-degradable material of the distal portion 3a there may be a shaft section featuring a backward cutting element allowing easier removal of the device at the end of the treatment.

Figure 6A:
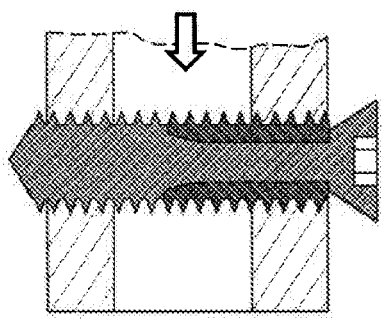
FIGS. 6a and 6b show the behavior of the screw-plate system according to the present invention in the immediate post-operative period.
Figure 6B:
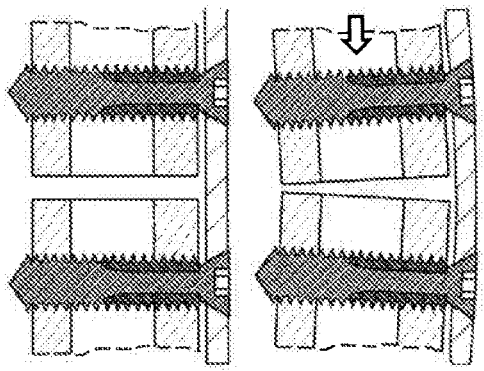

FIGS. 6a and 6b show respectively the mechanical behavior of a kit for the treatment of bone fractures comprising a plate and a plurality of devices for bone fixation during the very early stages of secondary fracture healing. In FIG. 6b, a long bone critical size defect and the immediate proximal and distal bone fragments are depicted. In the immediate post-operative period the kit behaves like a traditional system providing enough interfragmentary stability and a theoretical asymmetric fracture callus strain. In this case, there is not or a minor relative displacement between the near (cis) cortex and the screw symmetry axis.

Figure 7A:
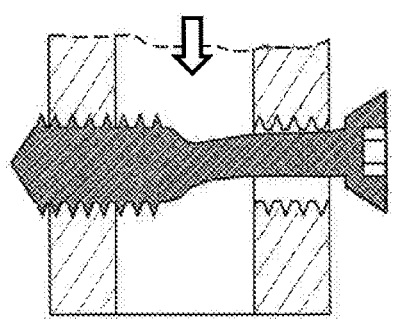
FIGS. 7a and 7b show the behavior of the screw-plate system according to the present invention once the resorbable portion of the device has lost its mechanical properties.
Figure 7B:
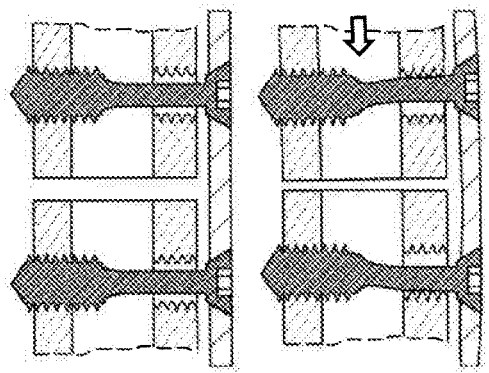

FIGS. 7a and 7b show respectively the mechanical behavior of a kit comprising a plate and a plurality of devices for bone fixation as the biologically degradable sleeves substantially lost their mechanical properties and/or are fully resorbed. The lack of support provided by the biologically degradable part of the device for bone fixation leads to an increased interfragmentary displacement. This is evident in particular in that portion of the callus between the near (cis) cortices of the two bone fragments.

For all the devices for bone fixation the allowed maximum relative displacement between the biologically non-degradable part of the device for bone fixation (core, proximal portion 3b) and the inner side of the bone hole in the near (cis) cortex, once the degradation of the material of the biologically degradable sleeve is completed, ranges preferably between 5 and 10% of the outer diameter $D_A$ of the thread of the distal portion 3a. The thickness of the biologically degradable sleeve and the degradation time of the sleeve can be however different according to the indication for use. The screw flexible length is proportional to the outer diameter of the thread of the distal portion of the device for bone fixation and depends on the baricenter of the applied load.

The provided table 1 below reports examples of 5% and 10% allowed displacements for some screws but it is not intended to be an exaustive description of all the possible characteristics of the device for bone fixation or limit in any way the scope of the invention. The dimentions of this device depends in fact on its intended use, constituent material and effect of the manufacturing processes.

TABLE 1

| Outer diameter of the thread of the distal portion of the device | Device length | Sleeve lenght | 5% max displacement | Biologically non-degradable core diameter | 10% max displacement | Biologically non-degradable core diameter |
| --- | --- | --- | --- | --- | --- | --- |
| 3.5 mm | 30 mm | 12 mm | ±.18 mm | 3.15 mm | ±.35 mm | 2.80 mm |
| 4.5 mm | 40 mm | 17 mm | ±.23 mm | 4.05 mm | ±.45 mm | 3.60 mm |

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

The invention claimed is:

1. A device for bone fixation, comprising: a head portion, a tapering front portion, and a shaft between said head portion and said tapering front portion, said shaft comprising a distal portion adjacent to said tapering front portion and a proximal portion adjacent to said head portion,
   wherein said distal portion comprises a thread, said distal portion further comprising a constant outer diameter $D_A$ and an inner core diameter $D_i$,
   wherein at least the proximal portion of said shaft comprises a core comprising a biologically non-degradable material with degradation rate BND and having a diameter $d \leq D_i$,
   wherein the device further comprises a sleeve surrounding said core and comprises a biologically degradable material with degradation rate BD, said sleeve having a diameter $Ds \leq D_A$,
   wherein BD>BND; and
   wherein said sleeve is fixed to said core in a non-rotatable manner.

2. The device for bone fixation according to claim 1, wherein said sleeve has a constant outer diameter $Ds<D_A$.

3. The device for bone fixation according to claim 1, wherein said sleeve has a constant outer diameter $Ds=D_A$.

4. The device for bone fixation according to claim 1, wherein d is less than $D_i$.

5. The device for bone fixation according to claim 1, wherein d is equal to $D_i$.

6. The device for bone fixation according to claim 1, wherein said sleeve comprises an outer thread.

7. The device for bone fixation according to claim 1, wherein said sleeve comprises a smooth outer surface.

8. The device for bone fixation according to claim 1, wherein a ratio d: $D_A$ is between 0.6 and 0.9.

9. The device for bone fixation according to claim 1, wherein the shaft comprises one or more biologically non-degradable materials selected from the group consisting of: titanium, titanium alloys (Ti-6Al-4V or Ti-6Al-7Ni), stainless steel, metal alloys (CoCr, CoCrMo, CoCrMoC, CoCrNi or CoCr—WNi), and long term biodegradable polymers.

10. The device for bone fixation according to claim 1, wherein said biologically degradable sleeve comprises a resorbable material.

11. The device for bone fixation according to claim 10, wherein the resorbable material comprises a material having an initial compression modulus in the range of 0.5-20.0 GPa.

12. The device for bone fixation according to claim 10, wherein a molecular weight, compression strength and elastic modulus of the resorbable material is reduced by 50% in a time period between four weeks and eight weeks, and by 90% in a time period between ten weeks and fourteen weeks.

13. The device for bone fixation according to claim 1, wherein the biologically degradable material of the sleeve comprises one or more of the following materials selected from the group consisting of:
   poly (glycolic acid) (PGA), polylactic acid (PLA) in its stereoisomeric forms that give rise to four morphologically distinct polymers (D,L,DL,meso), Poly(dioxanone) (PDS), poly-L-lactic-co-glycolic acid (PLGA), poly-D/L-lactic acid, poly-L-lactic acid, Poly(D,L-lactide-co-glycolide) acid, polycaprolactone (PLC), polycaprolactone-calcium phosphate (PCL-CaP), poly(L-lactide-co-D,L-lactide) (PLADLA or PLDLLA), and combinations thereof.

14. The device for bone fixation according to claim 1, wherein the biologically degradable material of the sleeve comprises one or more of the following materials:
   copolymeric lactic glycolic acid at different ratios, degradable self-expanding poly-L,D-Lactide and poly-ε-caprolactone homopolymers.

15. The device for bone fixation according to claim 1, wherein the thread of the distal portion is not continuous.

16. A kit for the treatment of bone fractures, comprising:
   a bone fixation device according to claim 1; and
   a bone plate comprising at least one locking plate hole comprising a locking mechanism configured to allow a stable fixation of the device for bone fixation within the bone plate.

* * * * *